(12) United States Patent
Tucker

(10) Patent No.: US 8,597,260 B2
(45) Date of Patent: Dec. 3, 2013

(54) CATHETER WITH DIRECTION ORIENTATION

(75) Inventor: David Jason Tucker, Walpole, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 3473 days.

(21) Appl. No.: 11/012,824

(22) Filed: Dec. 16, 2004

(65) Prior Publication Data

US 2006/0135915 A1    Jun. 22, 2006

(51) Int. Cl.
*A61M 1/00* (2006.01)

(52) U.S. Cl.
USPC .......................................... 604/272; 604/158

(58) Field of Classification Search
USPC ................. 604/500, 272–279, 158–163, 604/164.01–170.03
See application file for complete search history.

(56) References Cited

U.S. PATENT DOCUMENTS

| | | |
|---|---|---|
| 4,601,713 A | 7/1986 | Fuqua |
| 4,617,019 A | 10/1986 | Fecht et al. |
| 4,920,980 A | 5/1990 | Jackowski |
| 5,522,807 A | 6/1996 | Luther |
| 5,554,136 A | 9/1996 | Luther |
| 5,569,182 A | 10/1996 | Twardowski et al. |
| 5,690,611 A | 11/1997 | Swartz |
| 5,700,252 A | 12/1997 | Klingenstein |
| 5,800,414 A | 9/1998 | Cazel |
| 5,817,071 A | 10/1998 | Dewindt et al. |
| 5,910,129 A | 6/1999 | Koblish et al. |
| 5,961,486 A | 10/1999 | Twardowski et al. |
| 6,146,373 A | 11/2000 | Cragg et al. |
| 6,190,357 B1 | 2/2001 | Ferrari et al. |
| 6,190,371 B1 | 2/2001 | Maginot et al. |

(Continued)

FOREIGN PATENT DOCUMENTS

| | | |
|---|---|---|
| CA | 2262256 | 8/1999 |
| JP | 9-285546 | 11/1997 |

(Continued)

*Primary Examiner* — Kevin C Sirmons
*Assistant Examiner* — Phillip Gray
(74) *Attorney, Agent, or Firm* — Louis Woo

(57) ABSTRACT

A regional anesthesia catheter used with a guide such as for example a needle cannula has a distal portion integrally connected to a main portion of the catheter by a junction portion that has a cross-sectional profile different from the distal and main portions, so as to predispose the distal portion of the catheter to move in a given direction when the distal portion is not guided by or constrained by the needle cannula. The cross-sectional profile of the junction portion may be configured in a particular shape, or be constructed to have a flexibility that predisposes the distal portion to bend, curve or move toward a given direction. Once the predisposed direction to which the distal end of the catheter points is known, a physician can readily orient the catheter relative to the needle cannula so that once the distal end of the catheter exits the distal tip of the needle cannula, with the cannula already placed in a position proximate to the desired location to which the distal end of the catheter is to be placed, the physician can readily place the distal end of the catheter at the desired location within the patient. Instead of only one junction portion, a number of portions of a catheter may be configured to bend at a predefined direction. Further, a catheter may be configured to have a cross sectional profile or a predefined flexibility along its entire length that causes the catheter to bend, curve or move in a predefined direction.

16 Claims, 2 Drawing Sheets

(56) References Cited

U.S. PATENT DOCUMENTS

| | | |
|---|---|---|
| 6,217,527 B1 | 4/2001 | Selmon et al. |
| 6,290,692 B1 | 9/2001 | Klima et al. |
| 6,425,887 B1 * | 7/2002 | McGuckin et al. ........... 604/272 |
| 6,436,090 B1 | 8/2002 | Sanchez et al. |
| 6,524,302 B2 | 2/2003 | Kelly |
| 6,530,902 B1 | 3/2003 | Jonkman |
| 6,551,269 B2 | 4/2003 | Clemens et al. |
| 6,572,593 B1 | 6/2003 | Daum |
| 6,592,559 B1 | 7/2003 | Pakter et al. |
| 6,595,952 B2 | 7/2003 | Forsberg |
| 6,595,966 B2 | 7/2003 | Davey et al. |
| 7,163,524 B2 * | 1/2007 | Ishii ........................ 604/103.04 |
| 7,163,624 B2 | 1/2007 | Ishii |
| 2003/0004493 A1 | 1/2003 | Casey et al. |

FOREIGN PATENT DOCUMENTS

| | | |
|---|---|---|
| JP | 11-267224 | 10/1999 |
| JP | 2002-531229 | 9/2002 |
| JP | 2003-320032 | 11/2003 |
| JP | 2004-275786 | 10/2004 |

* cited by examiner

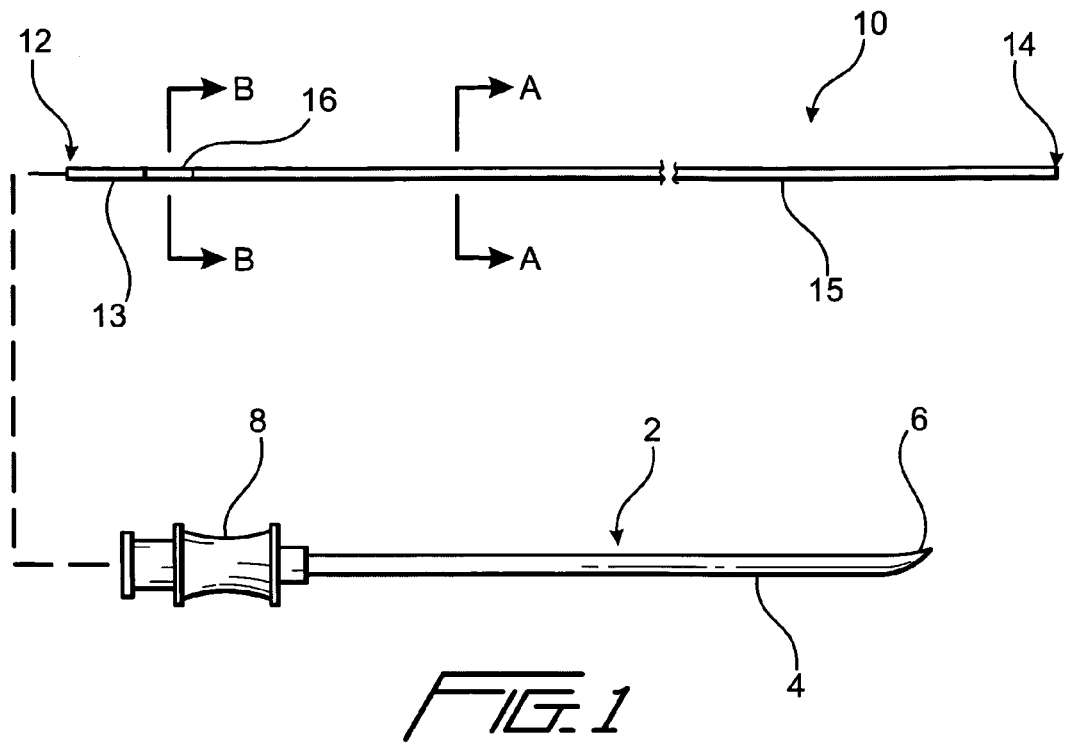
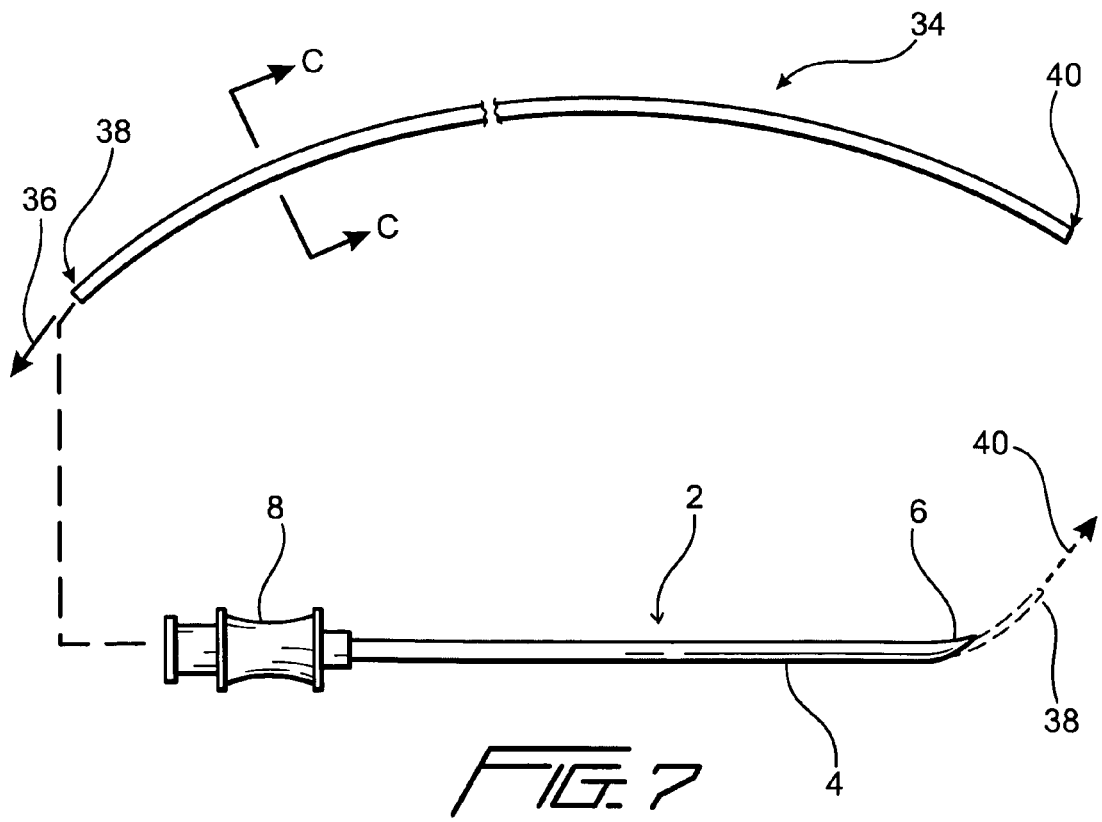

CATHETER WITH DIRECTION ORIENTATION

FIELD OF THE INVENTION

The present invention relates generally to catheters such as for example regional anesthesia catheters including epidural catheters that provide local anesthesia to a patient and more particularly to a catheter that has a built-in direction orientation that enhances the movement of the catheter to a particular location inside the patient.

BACKGROUND OF THE INVENTION

For regional anesthesia, a cathether such as an epidural catheter is used to introduce anesthetic agents to the nerves for example at the spine of a patient. To place a catheter close to the nerve spinal column, an epidural needle such as a Tuohy needle is used by the anaesthesiologist. The Tuohy needle is inserted into the nerve sheath, alongside a nerve plexus of the patient. The Tuohy needle has a sharp distal end that has a beveled aperture, the sharp distal end adapted to readily pierce the nerve sheath at the spinal column of the patient. Once the anaesthesiologist believes that she has placed the epidural needle at the appropriate location in the patient, she would insert the catheter into the needle and move the catheter until its distal end extends out from the beveled end of the needle cannula. The catheter is usually marked along its length so that the anaesthesiologist knows approximately how much the distal end of the catheter extends beyond the distal tip of the needle cannula. The direction in which the catheter is moved inside the patient depends, to a large extent, on the insertion and placement of the needle cannula inside the patient by the anaesthesiologist and the skill of anaesthesiologist in maneuvering the catheter. Oftentimes, an anaesthesiologist, experienced or not, may have a difficult time maneuvering the distal end of the catheter to the desired location. As a result, a larger than necessary dose of anesthetic agent may be required to be delivered to the patient to locally anaesthetize the patient.

There is therefore a need to provide a catheter that can readily be maneuvered by the physician to a desired location inside a patient.

SUMMARY OF THE PRESENT INVENTION

To assist a physician or an anaesthesiologist with the placement of a catheter for supplying local anesthetic to a patient, the catheter of the instant invention has at a portion proximate to its distal end, whereby anesthetic agent is output to a patient, a cross-sectional profile that predefines or predisposes the distal end of the catheter to be bent or headed to a given direction, once the catheter is no longer constrained by the guide or needle cannula wherethrough it passes. Conventionally, a catheter usually has a uniform circular cross sectional configuration throughout. For the instant invention, at least one portion of the catheter, preferably at a distance proximate to the distal end of the catheter, is configured to have a cross-section, which may or may not be circular, that predefines or predisposes the distal end of the catheter to move in a given direction. One of the cross-sectional profiles that may be used is an oval shaped configuration that causes, or predisposes, the catheter to be bent in the direction of the width of the greater cross-section width. Another sectional profile that may be used at the one portion of the catheter is C-shaped so that the distal end of the catheter is predisposed to bend toward the direction represented by the open mouth of the C.

In addition to having different cross-sectional profiles, the one portion that is configured to cause the distal end of the catheter to bend at a distal direction could have a different thickness at a section thereof so that, even though from the outside diameter the catheter may appear to be no different from the rest of the catheter, the inside diameter at the one portion is dimensioned to have thicker and thinner sections so that, once the one portion is outside of the needle cannula or guide, subject to additional movement, the catheter would tend to bend at a predefined orientation to a given direction, thereby enhancing the movement of the distal end of the catheter inside the patient.

The instant invention therefore relates to a catheter to be used with and passable through a guide for insertion to a patient. The catheter includes a tubing that has at least one portion having a cross-sectional profile that is configured to bend or orient the tubing in a given direction so that when the one portion of the tubing extends out of the guide, the tubing is predisposed to be routed or headed in a given direction.

The instant invention also relates to a combination of a hollow guide and a catheter passably fitted to and moveable along the guide. The catheter has a substantially circular cross-sectional profile along its entire length except for at least one portion between its distal and proximal ends. This one portion has a cross-sectional profile configured to predispose the distal end of the catheter toward a given direction so as to cause the catheter to move toward the given direction once the one portion of the catheter is no longer constrained by the guide.

The instant invention further relates to a catheter that has a distal portion connected to a main portion by a junction that has a cross-section that is different from the respective cross-sections of the main and distal portions. The distal portion, if unguided, points to and is movable along a first direction; and the main portion, if unguided, would point to and is movable along a second direction not in alignment with the first direction. The catheter is insertable into and movable along a hollow guide extending along a given axis. The junction that connects the distal portion with the main portion is configured to have a cross-sectional profile that causes the distal portion to bend or head toward the first direction once the distal portion and the junction are no longer confined within the guide after the catheter has been inserted to the guide and moved therealong.

The instant invention yet further relates to an apparatus that comprises a needle cannula and a regional anesthesia catheter such as an epidural catheter having a distal end and a proximal end. The catheter is movably fitted to the cannula with its distal end being inserted first into the first end of the cannula so that the catheter is movable along the cannula. The catheter has a substantially circular cross-section along its entire length except for at least one portion proximate to its distal end. This one portion has a non-circular cross-section configured to cause the distal end of the catheter to move in a direction predefined by the configuration of the one portion when the distal end and then the one portion of the catheter exit outside the cannula through its distal end.

The instant invention moreover relates to a method for introducing a catheter into a patient in which a hollow cannula is provided. The catheter has at least one portion between its distal and proximal ends that is configured to cause the distal end of the catheter to be predisposably moved toward a direction not in alignment with the cannula when the one portion is not confined within or constrained by the cannula. The cannula is inserted into the patient proximate to a location where anesthesia is desired. A catheter is inserted into and moved along the cannula. The distal end of the catheter is first inserted into the cannula. Thereafter, the catheter is continuously moved into the cannula until at least the one portion of the catheter is extended beyond the distal end of the cannula to predisposedly move the distal end of the catheter to the desired placement within the patient.

Another embodiment of the instant invention features a catheter such as for example a regional anesthesia catheter that has a cross sectional profile that extends longitudinally along the entire length of the catheter. The cross sectional profile is configured to cause the catheter to move in a predefined direction. In particular, the catheter of this embodiment comprises a tubing passable through a guide for insertion into a patient, the tubing having a given length and the cross sectional profile of the tubing along its entire length is configured to cause the catheter to bend, curve or move in a given direction.

The cross sectional profile of the catheter of the instant invention at the one portion as noted above or along the entire length of the catheter may be configured to be oval shaped or C shaped, or other non-circular shapes for example. The cross sectional profile may also be configured to be partially concaved inwards toward the center axis of the catheter or tubing, or may have a section of the wall where its thickness is different from that of the rest of the catheter.

It is therefore an objective of the instant invention to provide a catheter that is configured to be moved in a predisposed direction inside the patient.

BRIEF DESCRIPTION OF THE FIGURES

The present invention will become apparent and the invention itself will be best understood with reference to the following description of the present invention taken in conjunction with the accompanying drawings, wherein:

FIG. 1 is a plan view of the catheter system of the instant invention showing a guide in the form of a needle cannula such as an epidural needle, and the regional anesthesia catheter of the instant invention that is to be fitted into and passes through the needle cannula;

FIG. 7 is a plan view of another embodiment of the instant invention catheter where the catheter is configured to have a cross sectional profile along its entire length that predisposes the entire catheter to be move in a predefined direction.

DETAILED DESCRIPTION OF THE INVENTION

With reference to FIG. 1, a hollow guide in the form of a regional anesthetic needle such as for example an epidural needle 2 is shown to include a cannula 4 that has a beveled distal tip 6 having an aperture, not shown. Cannula 4 extends from distal tip 6 to, and through, a needle hub 8, which for discussion purposes may be considered to be the proximal end of needle cannula 4. Needle 2 may be a Tuohy needle, but not necessarily so for the operation and understanding of the instant invention. Needle hub 8 is made of a rigid plastic that enables the anesthesiologist to manipulate the needle cannula for insertion into a patient, for example into the nerve sheath, alongside a nerve plexus of the patient.

Although FIG. 1 illustrates an apparatus that comprises an epidural catheter and a needle guide in the form of an epidural needle cannula, it should be appreciated that the instant invention is not limited to epidural catheters. Rather, the instant invention is directed to regional anesthetic catheters which may include, but not limited to, Peripheral Nerve Block catheters, Vascular Access catheters, CV catheters, PICC (Peripherally Inserted Central Catheters) lines, Ureteral catheters, IVF catheters, Oocyte Recovery Suction catheters and Cardiac catheters.

Figures 2, 3:
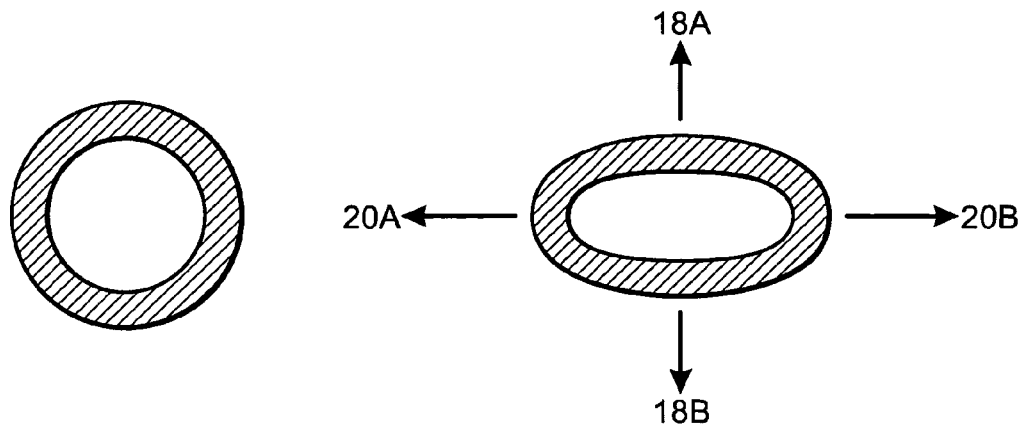
FIG. 2 is the cross-sectional view at A-A of the catheter of the instant invention.
FIG. 3 is the cross-sectional view B-B of the catheter of the instant invention.

Conventionally, a regional anesthesia catheter, such as for example the epidural catheter shown in the embodiment of FIG. 1, has a circular cross-section such as that shown in FIG. 2. Prior to the instant invention, to move a catheter to a desired location within a patient, after a needle cannula has been properly inserted into the patient, the physician has to manipulate the proximal portion of the catheter so as to gently guide the distal end of the catheter to the desired location in the patient. This manipulation of the catheter oftentimes requires a number of trials, even for experienced practitioners. Even when the physician is able to view the catheter, for example via an ultrasound viewing monitor, the placement of the distal end of the catheter nonetheless entails some degree of difficultly. This is possibly due to the fact that the distal end of the catheter, when inside the patient, would usually follow or go in the direction of the least resistance, as the physician moves the catheter.

Cannula 4 is adapted to receive a catheter 10. Catheter 10, which has a distal end 12 and a proximal end 14, is inserted into cannula 4 via its distal end 12 to the opening (not shown) formed by cannula 4 at hub 8. Catheter 10 is moved so that its distal end 12 passes through cannula 4, exiting at the latter's distal tip 6. Catheter 10 may be manufactured from materials such as but not limited to: nylon including polyamides, Teflon, PVC, urethane, silicone and polyolefins such as polypropylene, polyethylene and polybutylene.

In FIG. 1, catheter 10 is shown to include a distal portion 13 and a main portion 15 that are integrally connected by a junction portion 16. Portion 16 is located proximate to distal end 12 and has a cross-section that is different from the rest of the catheter, i.e., from both distal portion 13 and main portion 15. Distal portion 13 may be considered to extend from distal end 12 of catheter 10 to portion 16 while main portion 15 of catheter 10 may be considered to extend from portion 16 to proximal end 14 of the catheter. Albeit only one portion 16 is shown in the catheter of FIG. 1 embodiment, in practice, a number of portions 16 may be effected along the length of catheter 10 so that different predefined bends or curves may be configured in a single catheter.

When confined within a hollow guide, such as for example needle cannula 4, both the distal portion 13 and the main portion 15 of the catheter, being constrained by the cannula, are in alignment along the longitudinal axis defined by the needle cannula. However, when not confined or constrained, distal portion 13 of catheter 10 of the instant invention is not in alignment with its main portion 15, as portion 16 is configured to predisposedly position distal portion 13 out of alignment with main portion 15 of the catheter 10. Portion 16 of catheter 10 may also be configured to have a given flexibility that allows distal portion 13 and main portion 15 of catheter 10 to align along substantially the same longitudinal axis, so long as distal end 12 of catheter 10 does not come into contact with any obstruction. In other words, portion 16 may be configured to flexibly bend in a predisposed direction relative to main portion 15 of catheter 10 when distal portion 13 encounters an obstruction. Although shown as being only a part of catheter 10, portion 16 may in some iterations include the entire catheter.

As noted above, portion 16 of catheter 10 is configured to have a cross-sectional profile that is different from the rest of the catheter. For the FIG. 1 embodiment, the cross-section profile, per view B-B, may be in the shape of an oval, as shown in FIG. 3. With the oval shaped cross-section at portion 16, distal end 12 of catheter 10 is predisposed to move in either direction 18a or 18b, rather than 20a or 20b. Thus, in practice, when distal end 12, and then portion 16, of the catheter are moved beyond distal tip 6 of cannula 4, depending on the orientation of catheter 10, as it is being manipulated by the anesthesiologist, distal end 12 of the catheter may either go to the direction as indicated by 18a or the direction as indicated by 18b. This movement of distal end 12 in a given direction may be governed by the distal tip 6 of needle cannula 4 to a certain extent, as well as the orientation of catheter 10 as it was initially inserted into cannula 4.

In the event that obstruction is encountered, distal end 12 would bend in either direction 18a or direction 18b, depending on the orientation of the catheter, and the flexibility of the catheter at portion 16. Portion 16 of the catheter, which may be made from polyamide, may have a different thickness than that of the rest of the catheter. The difference in thickness may be effected during the extrusion process by stretching portion 16 more than the rest of the catheter. To effect an oval shape, portion 26 may be compressed by an appropriate tool after the catheter has been extruded or during extrusion. In any event, to effect the predisposed bending of the distal end 12 of the catheter relative to the remaining portion of the catheter, portion 16 may have a length from approximately 3 mm to 15 cm, depending on the length of the catheter.

Figures 4, 5:
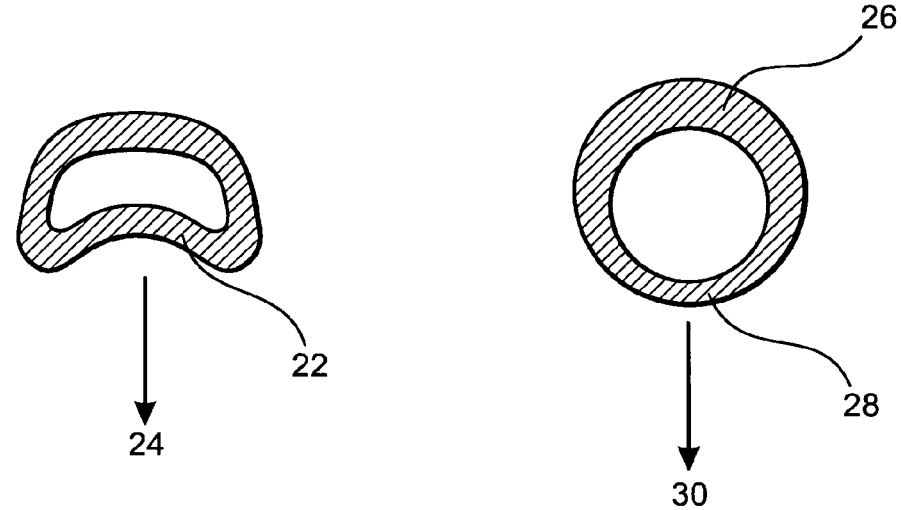
FIG. 4 is another cross-sectional view at B-B of the catheter of the instant invention.
FIG. 5 is yet another cross-sectional view at B-B of the catheter of the instant invention.

FIG. 4 shows another cross-sectional profile for portion 16 of catheter 10 of the instant invention. As shown, portion 16 has a cross-section in a shape of a C in which a section 22 of the catheter is constructed to have a concave shape toward the center of the catheter. As a consequence, distal end 12 tends to bend in the direction as shown by directional arrow 24. Depending on the flexibility built into portion 16, the bend may be a built-in curve where distal end 12 would not lie in alignment with the remainder portion of the catheter even when the catheter is not confined within a hollow guide such as for example needle cannula 4. Alternatively, the bend may be such that it only bends toward direction 24 when obstruction is encountered.

FIG. 5 shows yet another cross-sectional profile of portion 16 of the catheter of the instant invention. In this embodiment, the cross-section is configured to be thicker at section 26 and thinner at section 28. As a consequence, section 28 is more flexible, or pliable, than section 26 at portion 16. Thus, for the embodiment of FIG. 5, distal end 12 of the catheter is predisposed to move in the direction as indicated by directional arrow 30.

Figure 6:
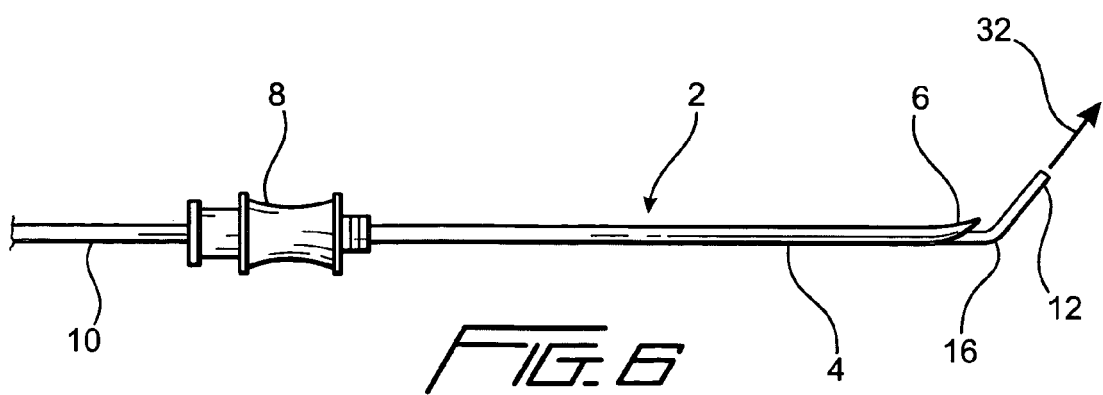
FIG. 6 is a plan view showing the distal end of the catheter of the instant invention having been extended outside the distal tip of the needle cannula through which the catheter of the instant invention is fitted and guidedly moved.

FIG. 6 shows the apparatus of the instant invention in which catheter 10 has been inserted into epidural needle 2 and moved such that its distal end 12 and portion 16 extend out of distal tip 6 of cannula 4. No longer being constrained by cannula 4, for the embodiment shown in FIG. 6, distal end 12 of catheter 10 curves toward the direction indicated by directional arrow 32, due to portion 16 having been configured to have a cross-sectional profile that predisposes distal end 12 to point toward direction 32, once distal end 12 and portion 16 are no longer confined within cannula 4.

In operation, a physician is provided with a hollow guide, such as needle cannula 4. The cannula is inserted into the patient proximate to a desired location where the catheter is to be placed. The catheter, and more particularly the distal end of the catheter, is inserted into the needle cannula and moved therealong, so that distal portion 13, portion 16, and main portion 15 of catheter 10 are confined within the cannula and are therefore in alignment along the longitudinal axis of the cannula. The catheter is moved further until distal end 12, and then portion 16, exit distal tip 6 of cannula 4. The orientation of distal end 12 of catheter 10, relative to cannula 4, is rotatably adjusted or oriented by the physician prior to her inserting the catheter into the cannula so that the distal end of the catheter would exit from the distal tip of the cannula in the direction of the desired location in the patient.

FIG. 7 is a plan view illustrating another embodiment of the catheter of the instant invention. Insofar as the needle cannula to be used with the catheter of the FIG. 7 embodiment is the same as the needle cannula shown in FIG. 1, no further discussion thereof is needed.

For the catheter 34 of the FIG. 7 embodiment, note that the entire length of the catheter is configured, per cross-section view C-C, with a cross-sectional profile that may be represented, for example, by any one of the profiles shown in FIGS. 3, 4 and 5. In addition to, or as an alternative of, the catheter of FIG. 7 may have along its entire length a section configured to have a flexibility characteristic that is different from the other sections of the catheter. With any one of the non-circular cross-sectional profiles as shown in FIGS. 3-5 and/or the flexible cross-section, catheter 34, as shown in FIG. 7, may have a naturally curved or biased orientation, even when the catheter is at rest and not being constrained or confined within the needle cannula 4. Putting it differently, catheter 34 of the FIG. 7 embodiment is configured to bend or move in the predefined direction as indicated by directional arrow 36. Thus, when catheter 34 is inserted into needle cannula 4, assuming that it remains oriented in the position as shown in FIG. 7, when it is moved by the physician and its distal end exits distal tip 6 of needle cannula 4, catheter 34 would move in the direction designated by directional arrow 40, as the distal portion of catheter 34, shown by dotted line, is naturally biased to and therefore is movable in the predefined direction. Catheter 34 thereby enabling the physician to readily place the distal end 38 of the catheter at the desired location within the patient for the supplying the anesthetic agent to the patient.

Although the catheter of the instant invention has been described thus far as used for supplying an anesthetic agent to a patient, it should be noted that other treatment agents may also be supplied via the inventive catheter. Such other treatment agents may include for example electrical energy, radio frequency (RF), microwave and ultrasound waves that may be transmitted by the catheter. In the case of electrical energy, it is envisioned that the catheter may be imbedded with an electrical conductive material such as carbon or includes a wire extending along its length.

It should be appreciated that the present invention is subject to many variations, modifications and changes in detail. Thus, it is the intention of the inventor that all matters described throughout this specification and shown in the accompanying drawings be interpreted as illustrative only and not in a limiting sense. Accordingly, it is intended that the invention be limited only by the spirit and scope of the hereto appended claims.

The invention claimed is:

1. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein the cross sectional profile of said tubing is circular except at said one portion.

2. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein the cross sectional profile of said one portion of said tubing is oval shaped.

3. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said one portion is approximately 3 mm to 15 cm in length proximate to a distal end of said tubing.

4. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said guide comprises a needle cannula for insertion into the patient, and said catheter comprises a regional anesthesia catheter insertable into and passing through said cannula for applying an anesthetic or other treatment agent to a selected region of the patient.

5. Catheter of claim 4, wherein said other treatment agent comprises any of electrical energy, RF, microwave and ultrasound waves.

6. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said one portion comprises a non-circular cross section configured to cause said tubing to bend at said one portion once said one portion is outside of and not constrained by said guide so that said catheter can readily be moved to a desired location within the patient.

7. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said guide comprises an epidural needle for insertion into the spine of the patient.

8. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said one portion of said tubing has at least one section that has a wall thickness less than that of the rest of said tubing.

9. A catheter to be used with and passable through a guide for insertion into a patient, comprising: a tubing having at least one portion having a cross sectional profile that is configured to bend the tubing in a given direction so that when said one portion of said tubing extends out of said guide, said tubing is bent so as to be routed in said given direction, wherein said one portion is configured to have a flexibility that is different from that of the rest of said catheter.

10. In combination, a hollow guide, a catheter passably fitted to and movable along said guide, said catheter having a substantially circular cross sectional profile along its entire length except for at least one portion between its distal and proximal ends, said one portion having a cross sectional profile configured to predispose the distal end of said catheter toward a given direction so as to cause said catheter to be moved in said given direction once said one portion of said catheter is not constrained by said guide, wherein the cross sectional profile of said one portion is oval shaped.

11. In combination, a hollow guide, a catheter passably fitted to and movable along said guide, said catheter having a substantially circular cross sectional profile along its entire length except for at least one portion between its distal and proximal ends, said one portion having a cross sectional profile configured to predispose the distal end of said catheter toward a given direction so as to cause said catheter to be moved in said given direction once said one portion of said catheter is not constrained by said guide, wherein said guide comprises a needle cannula for insertion into the patient, and said catheter comprises a regional anesthesia catheter insertable into and passes through said cannula for applying an anesthetic or other treatment agent to a selected region of the patient.

12. Catheter of claim 11, wherein said other treatment agent comprises any of electrical energy, RF, microwave and ultrasound waves.

13. In combination, a hollow guide, a catheter passably fitted to and movable along said guide, said catheter having a substantially circular cross sectional profile along its entire length except for at least one portion between its distal and proximal ends, said one portion having a cross sectional profile configured to predispose the distal end of said catheter toward a given direction so as to cause said catheter to be moved in said given direction once said one portion of said catheter is not constrained by said guide, wherein said one portion comprises a non- circular cross section configured to cause said catheter to bend at said one portion once said one portion is outside of and not constrained by said guide so that said catheter can readily be moved to a desired location within the patient.

14. In combination, a hollow guide, a catheter passably fitted to and movable along said guide, said catheter having a substantially circular cross sectional profile along its entire length except for at least one portion between its distal and proximal ends, said one portion having a cross sectional profile configured to predispose the distal end of said catheter toward a given direction so as to cause said catheter to be moved in said given direction once said one portion of said catheter is not constrained by said guide, wherein said one portion of said catheter has at least one section that has a wall thickness less than that of the rest of said catheter.

15. A catheter comprising a distal portion connected to a main portion by a junction that has a cross section different from the respective cross sections of said main and distal portions, said distal portion if unguided points to and is movable along a first direction and said main portion if unguided points to and is movable along a second direction not in alignment with said first direction, said catheter insertable into and movable along a hollow guide extending along a given axis, said junction being configured to have a cross sectional profile that causes said distal portion to bend toward said first direction once said distal portion and said junction are no longer confined within said guide after said catheter has been inserted into said guide and moved therealong.

16. Catheter of claim 15, wherein said guide comprises a cannula, and said catheter comprises a regional anesthesia catheter insertable into and passes through said cannula for applying an anesthetic to a selected region of the patient.

\* \* \* \* \*